United States Patent
Stierman

(10) Patent No.: US 8,900,227 B2
(45) Date of Patent: Dec. 2, 2014

(54) SINUS ABLATION DEVICES, METHODS, AND SYSTEMS

(76) Inventor: Karen Stierman, Austin, TX (US)

(*) Notice: Subject to any disclaimer, the term of this patent is extended or adjusted under 35 U.S.C. 154(b) by 1002 days.

(21) Appl. No.: 12/985,510

(22) Filed: Jan. 6, 2011

(65) Prior Publication Data

US 2012/0179158 A1    Jul. 12, 2012

(51) Int. Cl.
*A61B 18/18* (2006.01)
*A61B 18/14* (2006.01)
*A61B 18/00* (2006.01)
*A61B 17/24* (2006.01)

(52) U.S. Cl.
CPC ... *A61B 18/1485* (2013.01); *A61B 2018/00327* (2013.01); *A61B 2018/0016* (2013.01); *A61B 2018/00267* (2013.01); *A61B 2018/00982* (2013.01); *A61B 2218/002* (2013.01); *A61B 2017/246* (2013.01); *A61B 2018/00583* (2013.01); *A61B 2018/00244* (2013.01)
USPC .......................................................... 606/41

(58) Field of Classification Search
CPC ................. A61B 18/1485; A61B 2018/00327; A61B 2018/00244; A61B 2018/00267; A61B 2018/00982; A61B 2018/0016; A61B 2018/00583; A61B 2018/00577; A61B 2018/00226
USPC .......................................................... 606/41
See application file for complete search history.

(56) References Cited

U.S. PATENT DOCUMENTS

| | | | |
|---|---|---|---|
| 5,156,151 A | 10/1992 | Imran | |
| 5,255,679 A | 10/1993 | Imran | |
| 5,558,073 A | 9/1996 | Pomeranz et al. | |
| 6,036,689 A | 3/2000 | Tu et al. | |
| 6,190,381 B1 | 2/2001 | Olsen et al. | |
| 7,704,248 B2 | 4/2010 | DiCarlo | |
| 2003/0144659 A1* | 7/2003 | Edwards | 606/41 |
| 2005/0240147 A1* | 10/2005 | Makower et al. | 604/96.01 |
| 2007/0129751 A1* | 6/2007 | Muni et al. | 606/196 |
| 2008/0097295 A1* | 4/2008 | Makower et al. | 604/99.04 |
| 2008/0154250 A1* | 6/2008 | Makower et al. | 606/10 |
| 2009/0299355 A1 | 12/2009 | Bencini et al. | |

OTHER PUBLICATIONS

Ralph Metson, MD, "YAG Laser Endoscopic Sinus Surgery: A Randomized, Controlled Study," Jun. 1, 2009, 1 page.
Gerlinger, et al., "KTP-532 Laser-Assisted Endoscopic Nasal Sinus Surgery," Apr. 2003, 1 page.
Fischer, et al., Radiofrequency-Induced Thermotherapy on Nasal Polyps: Preliminary Results, May-Jun. 2006, 1 page.
Friedman, et al. "A Safe, Alternative Technique for Inferior Turbinate Reduction," 1999, pp. 1834-1837.
Slack, et al., "Functional Endoscopic Sinus Surgery," Sep. 1, 1998, pp. 1-12.
Hologic, Inc., "What Can I Expect From Novasure Procedure?" 2005-2010, 1 page.

(Continued)

*Primary Examiner* — Linda Dvorak
*Assistant Examiner* — Eunhwa Kim
(74) *Attorney, Agent, or Firm* — Trop, Pruner & Hu, P.C.

(57) ABSTRACT

An embodiment of the invention concerns systems, devices, and methods for minimally invasive sinus mucosal restorative techniques. Such an embodiment may remove persistent mucosal disease while protecting bony structures of sinus cavities from damage. For example, guard members may keep ablation electrodes a set distance away from sinus bone. This may preserve healthy tissue over the bone to thereby facilitate healing while ablating the disease tissue.

22 Claims, 6 Drawing Sheets

(56) References Cited

OTHER PUBLICATIONS

Rosenthal, et al., "Wound Healing in the Rabbit Paranasal Sinuses After Coblation Surgery," 1 page.

Radojicic, "Sinusitis," Aug. 1, 2010, pp. 1-10.

Rosenthal, et al., "Wound Healing in the Rabbit Paranasal Sinuses After Coblation: Evaluation for use in Endoscopic Sinus Surgery," May-Jun. 2009, pp. 1-2.

* cited by examiner

SINUS ABLATION DEVICES, METHODS, AND SYSTEMS

BACKGROUND

Sinusitis is inflammation of the sinuses, which are air-filled cavities in the skull lined by mucosa. The etiology can be infectious (bacterial, viral, or fungal) or noninfectious (allergic vs. reactive). Sinonasal mucosa responds to irritation by producing mucus and recruiting mediators of inflammation, such as white blood cells, to the lining of the nose and sinus, which cause congestion and swelling of the sinonasal passages. The resultant sinus cavity hypoxia and mucus retention cause the cilia—which move mucus and debris from the nose—to function less efficiently, creating an environment for bacterial and other infectious organisms to grow. If the acute sinusitis does not resolve, chronic sinusitis can develop from mucus retention, hypoxia and/or other changes in the gaseous environment of the sinus, and blockage of the ostia. This promotes mucosal hyperplasia, continued recruitment of inflammatory infiltrates (at times mixed with bacteria or fungus (biofilms)), potential for permanent damage to the cilia, and the potential development of sinonasal polyps, a projecting mass of swollen and hypertrophied tissue or other growths in the sinus (e.g., cysts).

If medical therapy fails to alleviate the sinusitis, endoscopic sinus surgery (ESS) may be performed to clear sinuses of chronic infection, inflammation, and polyps or other growths and aid in aeration of the sinus. ESS is a technique in which sinus air cells and sinus ostia are opened under direct visualization with, for example, an endoscope. (Versions of ESS may address opening the ostia of the sinus but do not address the numerous patients who suffer with persistent mucosal disease despite an open ostia.) The goal of ESS is to restore sinus ventilation and improve function of the lining of the sinus (e.g., address sinonasal dysfunctional lining). After suitable vasoconstriction using cocaine or oxymetazoline and 1 percent lidocaine with epinephrine, the uncinate process may be removed or medialized, exposing the ethmoid bulla and the opening called the hiatus semilunaris, into which the sinuses drain. Anterior and posterior ethmoid air cells may also be opened, allowing better ventilation. The maxillary ostium may be inspected and, if obstructed, opened by endoscopically enlarging it by either using conventional endoscopic sinus instruments or balloon driven technology to enlarge it. This then allows achieving a middle meatal antrostomy. The frontal and sphenoid sinuses can also be addressed by opening their ostia.

However, ESS may still fail to truly alleviate chronic and sometimes diffuse sinusitis. Also, complications of ESS can result in blindness resulting from damage to the eye and damage to the brain due to the proximity of these structures to the sinuses. Furthermore, ESS may unintentionally damage the mucosa and expose bone, thereby interfering with sinonasal physiology due to, for example, the removal or damage of cilia that help clear contaminants and fluids from the sinuses. Frequent sequelae of exposed bone include prolonged crusting with foul odor (biofilms) and sometimes bleeding. These conditions may put the patient at risk of bone infection. Therefore, minimally invasive techniques are needed to address sinonasal disease especially when it persists despite patent ostia.

In other words, sinus techniques may allow for sinuses to be opened up and for tissue to be removed. However, there is no minimally invasive technique that effectively treats, for example, persistent disease in sinuses, such as is seen frequently in the maxillary sinus. Current endoscopic techniques for removal of persistent mucosal disease involving use of powered endoscopic instrumentation (e.g., microdebrider) or other cutting/tissue removal instruments are problematic because they can lead to bone removal and/or exposure, which complicate sinus healing and can increase risk of infection (e.g., osteomyleitis). These current instruments also put the patient at higher risk for damage to adjacent structures (e.g., eye and brain as well as nerves and blood vessel inadvertent injury).

BRIEF DESCRIPTION OF THE DRAWINGS

Features and advantages of embodiments of the present invention will become apparent from the appended claims, the following detailed description of one or more example embodiments, and the corresponding figures, in which:

DETAILED DESCRIPTION

In the following description, numerous specific details are set forth. However, it is understood that embodiments of the invention may be practiced without these specific details. Well-known structures and techniques have not been shown in detail to avoid obscuring an understanding of this description. References to "one embodiment", "an embodiment", "example embodiment", "various embodiments" and the like indicate the embodiment(s) so described may include particular features, structures, or characteristics, but not every embodiment necessarily includes the particular features, structures, or characteristics. Further, some embodiments may have some, all, or none of the features described for other embodiments. Also, as used herein "first", "second", "third" describe a common object and indicate that different instances of like objects are being referred to. Such adjectives are not intended to imply the objects so described must be in a given sequence, either temporally, spatially, in ranking, or in any other manner. Also, the terms "coupled" and "connected," along with their derivatives, may be used. In particular embodiments, "connected" may be used to indicate that two or more elements are in direct physical or electrical contact with each other and "coupled" may mean that two or more elements co-operate or interact with each other, but they may or may not be in direct physical or electrical contact.

An embodiment of the invention concerns systems, devices, and methods for minimally invasive sinus mucosal restorative techniques. This embodiment could be part of a system of minimally invasive tools. Such an embodiment may remove persistent mucosal disease while protecting bone surrounding the sinus cavities from damage. For example, guard members may keep ablation electrodes a set distance away from sinus bone. This may preserve healthy tissue over the bone to thereby facilitate healing while ablating the disease tissue.

Figure 1:
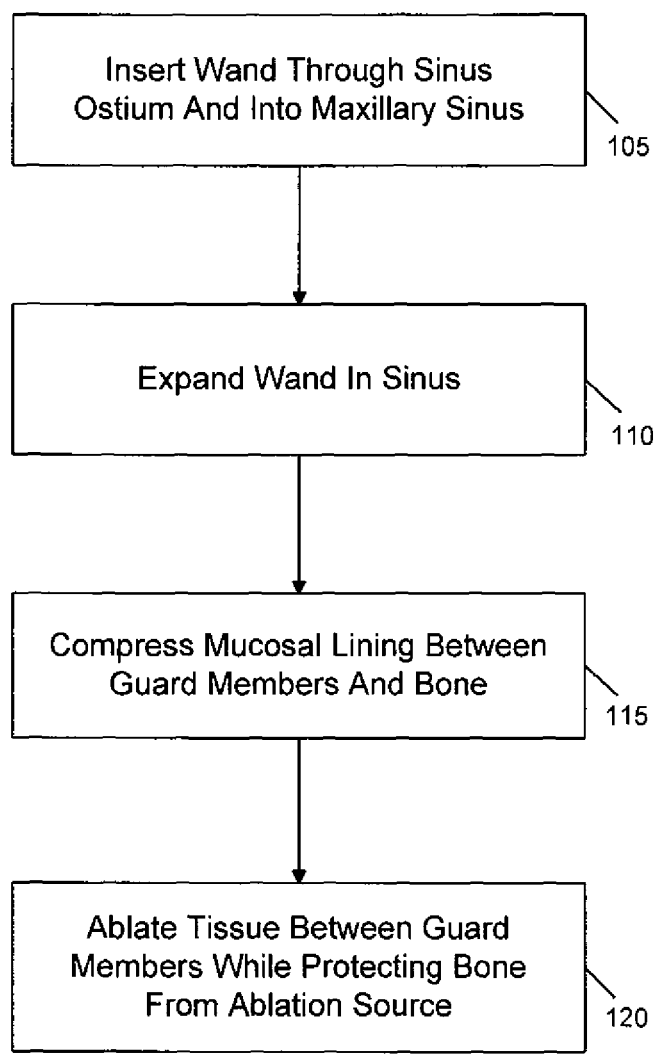
FIG. 1 includes a method for sinus ablation in an embodiment of the invention.
Figure 2:
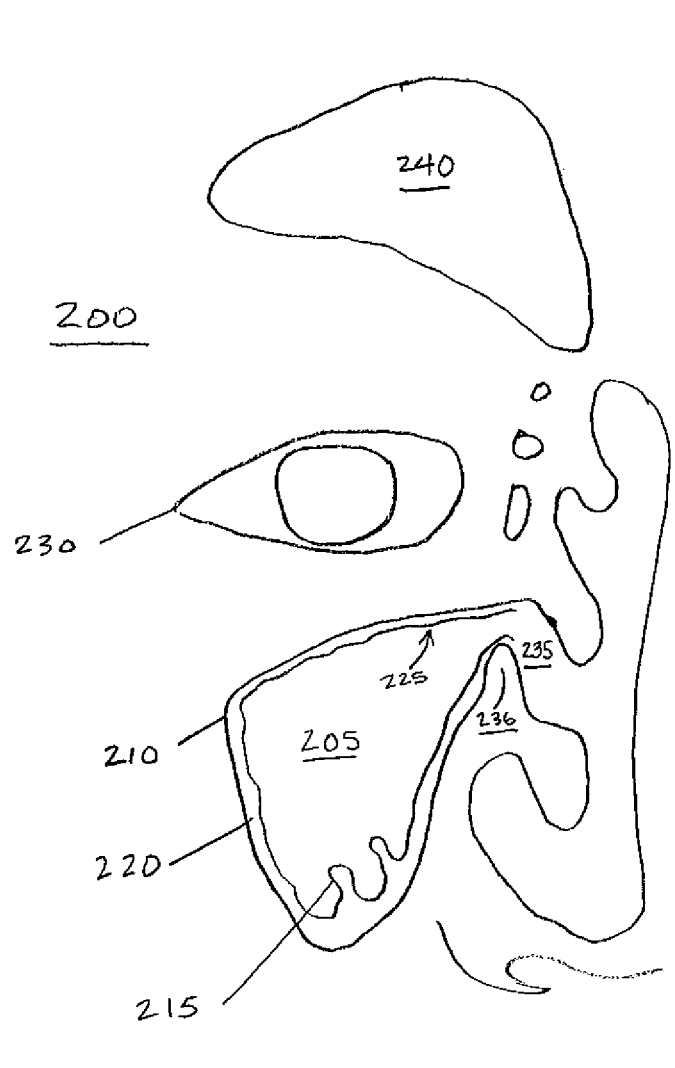
FIG. 2 depicts an example of sinus anatomy in a human.
Figure 3:
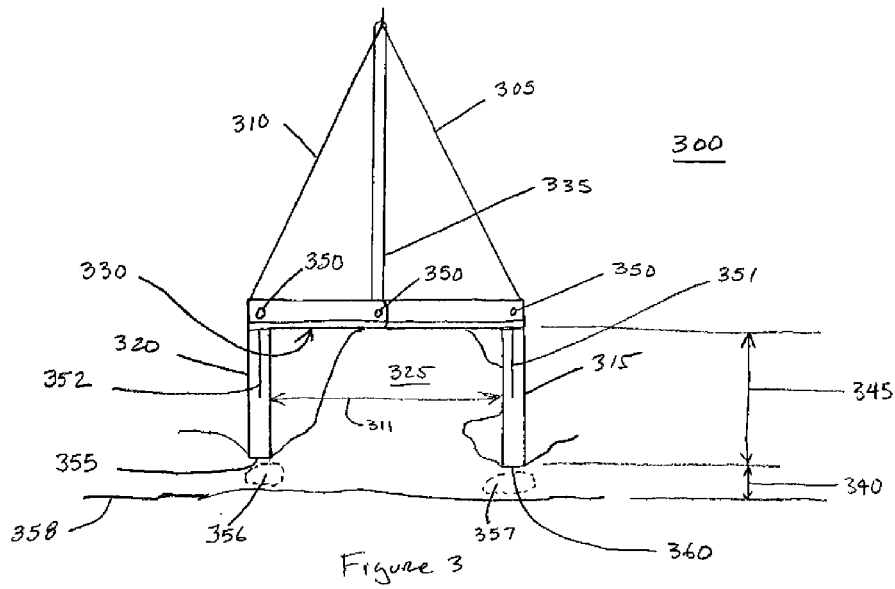
FIG. 3 includes an embodiment of the invention for sinus ablation.

FIG. 1-3 are now used to address an embodiment of the invention. Method 100 is for treating mucosal disease. In block 105 a user inserts wand or probe 335 into a patient's maxillary sinus 205 that has a diseased mucosal lining 220 covering bone 210. In block 110 the user expands wand 335 inside maxillary sinus 205 by deploying first 320 and second 315 guard members. These may be deployed in any number of ways. For example, members 320, 315 may pivot about pivots 350 from an unexpanded or undeployed position (where they are pivoted to essentially align with wand body 335) to an expanded or deployed position as seen in FIG. 3. To collapse the structure tethers 310, 305 may be withdrawn by the user thereby pivoting members 320, 315 about pivots 350. In an embodiment, tethers of sufficient rigidity may be used to deploy members 320, 315 as well. Other expansion/compression methods are included in various embodiments of the invention. For example, members 320, 315 may be composed of a shape memory polymer that expands under body heat, a resilient nitinol cage (e.g., that is located in a sheath and then projected out from the sheath to allow for expansion followed by withdrawal back into the sheath for removal), or other resilient compositions that may allow for expansion once deployed into a sinus.

In block 115 the user connects outer portions 355, 360 of the first and second guard members 320, 315 respectively with first 356 and second 357 portions of the mucosal lining to directly compress the first and second portions 356, 357 of the mucosal lining against bone 358 so a third portion 325 of the mucosal lining, which is not directly compressed by any guard member, lays between the compressed first and second portions 356, 357 of the mucosal lining.

In block 120, while compressing the first and second portions 356, 357 of the mucosal lining, the user may simultaneously ablate portion 325 of the mucosal lining with ablation electrode 330 while also maintaining the outer portions 355, 360 of the first and second guard members between an outer portion of the ablation electrode 330 and bone 358. Thus, the guards 320, 315 protect bone 358 from being harmed due to, for example, excessive ablation (e.g., due to bone being too close to ablation electrode). After an ablation, saline and suction may be introduced into the sinus and removed via one or more conduits or lumens included in or coupled to wand 335.

In an embodiment a user may insert wand 335 through the patient's sinus ostium 235, past the patient's still intact ucinate process 236, into maxillary sinus 205, and then ablate the diseased mucosal lining, such as polyp 215 or other chronically infected tissue. However, in other embodiments the ostium may have been previously widened due to sinuplasty, ESS, and the like. In an embodiment, wand 335 may be inserted using a Seldinger technique with corresponding introducer sheathes and the like.

As seen in FIG. 3, guard members 320, 315 may be separated from each other by a maximum breadth 311 that is less than the maximum breadth of ablation electrode 330. Thus, the electrode cannot pass between the guard members and ablate too closely to the bone. For example, guard members may include tracks or grooves 352, 351 that electrode 330 may travel down. Tracks 352, 351 may terminate at inner portions of the guard members which thereby stop electrode 330 from continuing towards tissue and bone 358.

Figure 4:
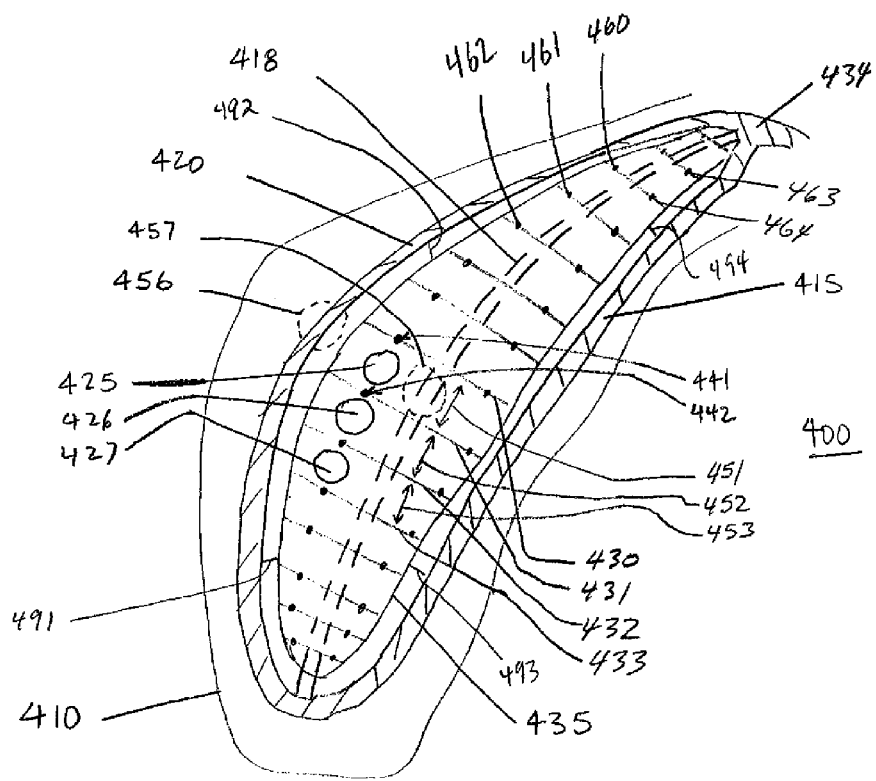
FIG. 4 includes an embodiment of the invention for sinus ablation.

FIG. 4 includes various combinations of embodiments of the invention for sinus ablation. Such embodiments may be used in conjunction with method 100 or using other methods.

A first guard member is included in spline 420, coupled to wand 434, and a second guard member is included in second spline 418, also coupled to wand 434. Additional splines may exist such as spline 415. Thus, splines 420, 418, 415 may form a basket. Four, five, six, seven, eight, nine, ten or more splines may be used. The basket may be compressed, nondeployed, or unexpanded upon entry into the maxillary sinus, and then decompressed, deployed, or expanded (see FIG. 4) once inside the sinus. As seen in FIG. 4, splines 420, 418 serve as first and second guard members that compress tissue at many locations, including locations 456, 457. This leaves tissue portion 425 uncompressed (at least partially). Splines 420, 418 (along with other structures such as members 430, 431) may be thought of as being included in a window (e.g., windows 451, 452, 452 along with others that are not individually numbered) through which portion 425 projects (at least partially) toward any ablation electrodes (e.g., 441, 442) while portion 425 is ablated. Electrodes (e.g., 441, 442, 460, 461, 462, 463, and 464 along with others that are not individually numbered) may be included on cross members (e.g., 430, 431, 432, 433 along with others that are not individually numbered).

Cross members (e.g., 430, 431) and electrodes (e.g. 441, 442) may be included in, for example, a resilient basket or other configurations. For example, in FIG. 4 cross members (e.g., 430, 431) and electrodes (e.g. 441, 442) are included on a surface of balloon 435. Balloon 435 may fully expand entirely within the expanded splines 420, 418, 415 and be prevented by inner portions of those same splines from expanding outside the outer portions of the splines. As a result, electrodes generally only contact tissue that projects through the aforementioned windows. In an embodiment, the splines may be 1-2 mm thick. In other embodiments, the splines may be 3, 4, 5, 6, 7, or 8 mm thick. Normal healthy mucosal lining may be 1-2 mm in thickness while diseased tissue may be 2, 3, 4, 5, 6, 7, 8 mm or more in thickness. Thus, the thicker diseased tissue may be squeezed between guard members (See FIGS. 3 and 4) and into contact with an electrode. As the splines are pressed into the lining, a 1-2 mm thick spline will ensure no electrode on substantially rigid balloon 435 gets less than 1-2 mm from bone 410.

In an embodiment, balloon 435 (or other internal basket or electrode delivery mechanisms) may be rotated by the user (while guard basket splines remain stationary) to ablate in different locations. In other embodiments, an electrode or series of electrodes may be included in a single internal spindle that can be rotated to ablate tissues in various locations.

To ablate tissue, energy may be supplied from any of the electrodes. For example, with bipolar ablation energy may be passed between from electrode 441 to 442, from 441 to 462, from 441 to a large reference electrode placed on the patient's body, and the like. With coblative ablation, saline may be supplied (e.g., via a conduit or lumen included in or coupled to wand 434) to carry energy between various electrodes (see, e.g., FIG. 5). Embodiments of the invention are not limited to any one form of ablation and may include, for example, bipolar ablation, coblation, cyroablation and the like where energy (e.g., current, heat) is use to disassociate, disrupt (e.g., molecular bonds), denature, destroy or harm tissue. In an embodiment, guard members may be low energy conducting insulators. For example, they may include ceramic, plastic, or other known insulators to protect bone 410 from harmful ablative energy (e.g., ensure harmful amounts of energy do not travel to bone via guard members themselves).

Also, in one embodiment any of the electrodes may be used for sensing. For example, system 500 (FIG. 7) may be used not only for programmed ablation (e.g., selecting current levels and ablation paths between electrodes) but also for sensing. Specifically, the system may sense an ablation electrode (e.g., 441) is in contact with tissue before ablating the same tissue. Any number of sensing methods may be used and various embodiments use basic resistance and/or inductance testing between any two electrodes (e.g., 441, 442) for sensing. Thermal sensors and corresponding sensing, along with other forms of sensing, are included in various embodiments.

In an embodiment, such sensing may be used to ensure tissue has been sufficiently ablated. For example, tissue resistance may change after it has been adequately ablated. Such sensing may also be used to determine depth of ablation. For example, electrodes may be included at varying levels in the guard members (e.g., 571, 572, 573, 574, 575, 576, 577, and 578). Thus, conduction between electrodes 578 and 574 at a higher level than conduction at electrodes 575 and 571 (or any other depth electrodes that may be in contact with ablated tissue) may alert the user that likely healthy tissue near bone is still intact while likely diseased tissue further away from tissue has been sufficiently ablated.

Figure 6:
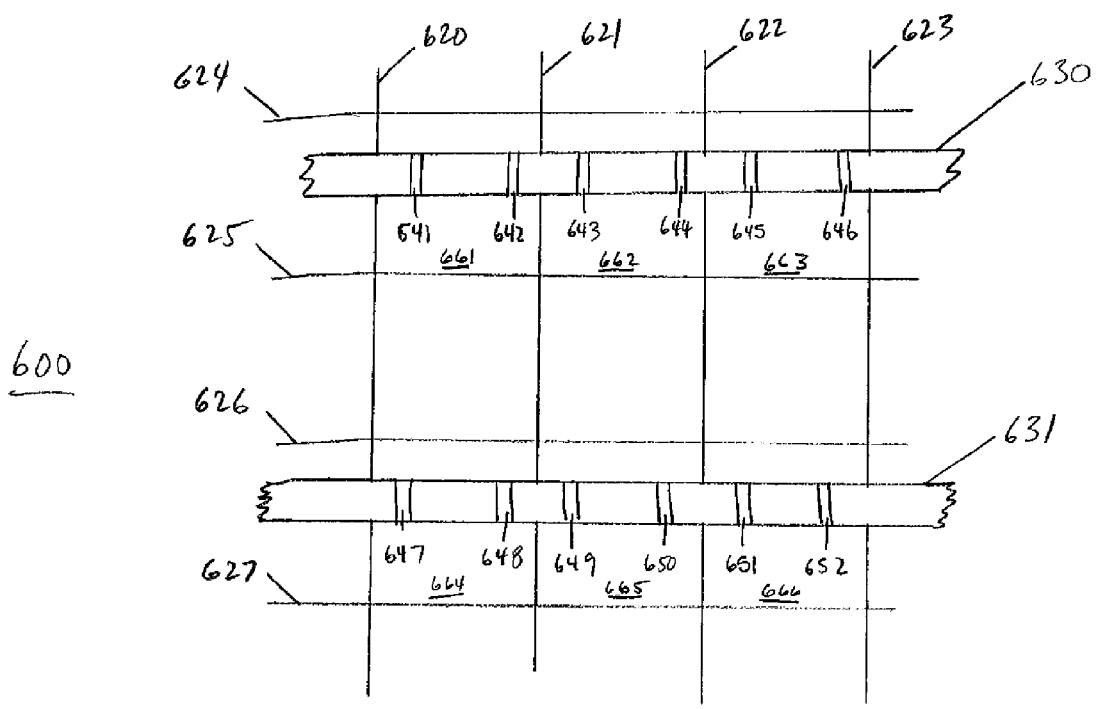
FIG. 6 includes an embodiment of the invention for sinus ablation.

In an embodiment, guard members are included in a mesh that is deployed or expanded after insertion into a sinus cavity. FIG. 4 includes a mesh of sorts comprised of struts or splines 420, 418, 415 (and other not specifically drawn) and cross members (e.g., 430, 431, 432, and 433). FIG. 6 includes another mesh comprised of interlaced horizontal and vertical guard members 620, 621, 622, 623, 624, 625, 626, 627, all of which may be of sufficient thickness (e.g., 2 mm) to create a protective barrier between bone and members 630, 631 and any or all of electrodes 641, 642, 643, 644, 645, 646, 647, 648, 649, 650, 651, 652 located on members 630, 631. Such a mesh may be composed of a shape memory polymer that expands under body heat, a nitinol cage, or other resilient compositions that may allow for expansion of the mesh once deployed into a sinus. Such a mesh may be delivered, compressed or undeployed, to the sinus in a sheath or conduit from which it may be ejected to allow for expansion.

In an embodiment, various guards, crossmembers, and structures included in or coupled to a wand may include radio opaque markers to help facilitate visualization and placement of the system.

In an embodiment, system 600 may include square or rectangular windows 661, 662, 663, 664, 664, 666 that are each approximately 2 mm by 2 mm. However, other embodiments may include windows of other dimensions such as 1 mm by 1 mm, 3 mm by 3 mm, 4 mm by 4 mm, and the like, and combinations thereof that include non-rectangular windows to accommodate different anatomies and/or conditions (e.g., large or small polyps, diffuse or non diffuse diseased tissue). In other words, the window size may be controlled, along with rigidity of members 630, 631, to ensure enough space is provided to allow diseased tissue to squeeze through a window (and towards an ablative electrode) while small enough to ensure members 630, 631 do not bend through the window and too close to bone.

Regarding FIG. 4, the maximum size of the electrode balloon, electrode basket, and the like may be sized so that at maximum expansion the device is smaller than the anticipated size of the sinus cavity. Thus, the device is not entirely reliant upon outer guard members to keep electrode members from getting too close to bone. Also, in the various embodiments the guard members may be coupled to the electrode balloon. In other words, regarding FIG. 4, expanding the splines does not necessarily have to occur separate and apart from expanding the electrode or electrode array. For example, guard splines may affix (e.g., via members 491, 492, 493, 494) to balloon 435 similar to how the electrode array affixes to the balloon. Thus, when balloon 435 (or a basket, etc.) is expanded, so too are the guards. Thus, the balloon can be expanded to substantially fill the sinus (or at least contact walls) knowing the guard members will still keep electrodes a safe distance from bone. An ablation or ablations (or simultaneous ablations) may be performed. Then the balloon partially collapsed, rotated, and then expanded again. An additional ablation or ablations (or simultaneous ablations) may then be performed. The guards do not need to be splines but could be bars, legs, projections, donuts that encircle electrodes, and the like.

Figure 5:
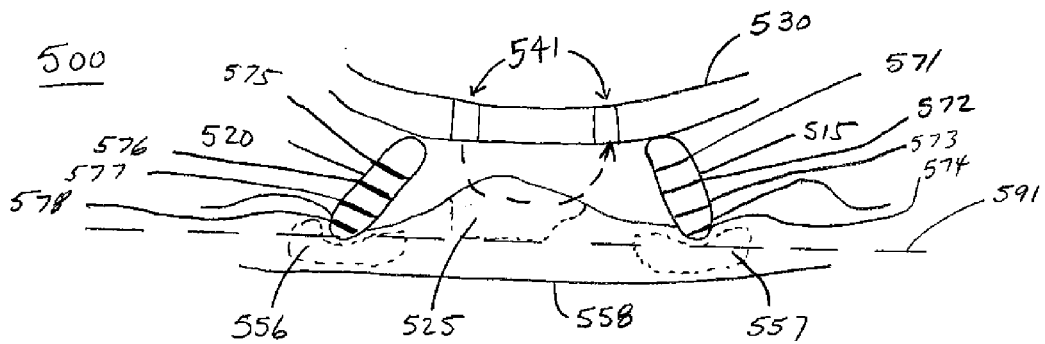
FIG. 5 includes an embodiment of the invention for sinus ablation.

FIG. 5 includes an embodiment of the invention wherein tissue 525 is squeezed or projected up "between" guard members 520, 515 while outer tips of guard members 520, 515 remain "between" electrodes 541 and bone 558. Tissue 525 is projected towards electrodes 541 but not in contact with the electrodes. Such an embodiment may rely on coblation (see dashed arrow for ionized saline energy path), for example. Compressed tissues 556, 557 partially surround tissue 525 to be ablated. In an embodiment, electrodes 541 may be included in a cross member that is of sufficient rigidity to be expandable but also to stiff to significantly bend between guard members 515, 520.

In an embodiment wand 335, 434 may include a sinuplasty balloon or other minimally invasive device which may be expanded in the patient's sinus ostium 235 to expand the sinus ostium to provide for aeration or draining of sinus 205 and/or provide easier entry into the sinus for wand 335, 434.

In an embodiment, a user may press ablation electrodes 541 and member 530 against inner portions of the guard members 520, 515 while ablating the portion 525 of the mucosal lining. However, in some embodiments contacting ablation electrodes 541 or crossmember 530 to either of guard members 520, 515 may automatically discontinue ablation of tissue as electrodes 541 may be thought to be too close to bone 558. Sensing such contact between ablation electrodes 541 or crossmember 530 to either of guard members 520, 515 may be determined based on sensors that detect, for example, a decrease or change in resistance or impedance between guard members 520, 515 due to a conductive path included in member 530 electrically coupling guard members 520, 515 to one another.

As seen in FIG. 6, a user may expand the wand inside the maxillary sinus by deploying guard members (e.g., 620, 621, 622, 623, 624, 625) that simultaneously compress directly underlying tissues to thereby project other tissues (e.g., polyps or inflamed and swollen tissue) into square windows 661, 662, 663 (formed by guard members 620, 621, 622, 623, 624, 625). While under compression, a user may simultaneously (a) use electrodes 641, 642 to ablate tissue within window 661 and (b) electrodes 645, 646 to ablate tissue within window 663. In some embodiments a single electrode may stretch across several windows to provide simultaneous ablation across multiple windows or other areas of tissue. Such varying ablation areas or windows may be collectively included in a diffuse diseased mucosal lining. Thus, treatment of diffuse disease may be simplified due to the ability to created wide spread ablation areas in less time due to simultaneous ablation sites.

In an embodiment, a user may ablate different areas at different energy levels. For example, one ablation area may be located away from the superior sinus wall (and nerves related to the eye) at a first energy level and another ablation area may be located along the superior sinus wall. The area near the superior sinus wall may be ablated at a lower energy level than the other area. The areas may be ablated simultaneously or nonsimultaneously.

In one embodiment, tissue is ablated without aid of simultaneous endoscopic visualization. Indirect visualization could occur with, for example, c-arm radiographic techniques or by transillumination techniques with inserting a light in the sinus. This may be of particular import in sinus ablations where access to the sinus is often difficult. In various embodiments, the guard members may be included in a monolithic device. For example, in FIG. 3 guard members 320, 315 may be included in a circular guard member wherein member 320 constitutes a half of the circular guard and member 315 constitutes another half of the circular member. The guard member, composed of smaller guard members, may have a tissue contact profile this is circular, ovoid, elliptical, square, and the like.

In various embodiments, a mesh may not necessarily fill the entire sinus. A mesh may instead be formed like a spoon or probe wherein the user can direct ablations at specific portions of the sinus. A user may first ablate by placing the guard mesh along the inferior maxillary sinus wall and then ablating rigorously in that area where large disease tissue may exist. The user may then reposition the mesh to the superior maxillary sinus wall and ablate there, possibly less rigorously (e.g., lower energy level, lower burn duration, different energy frequency, and the like) taking proximity to the eye into account.

Various embodiments may be designed for various sinus cavities including, without limitation, any of the maxillary, ethmoid, sphenoid, and frontal sinus cavities along with other areas such as the along any of the turbinates, nasal septum, and the like.

Figure 8:
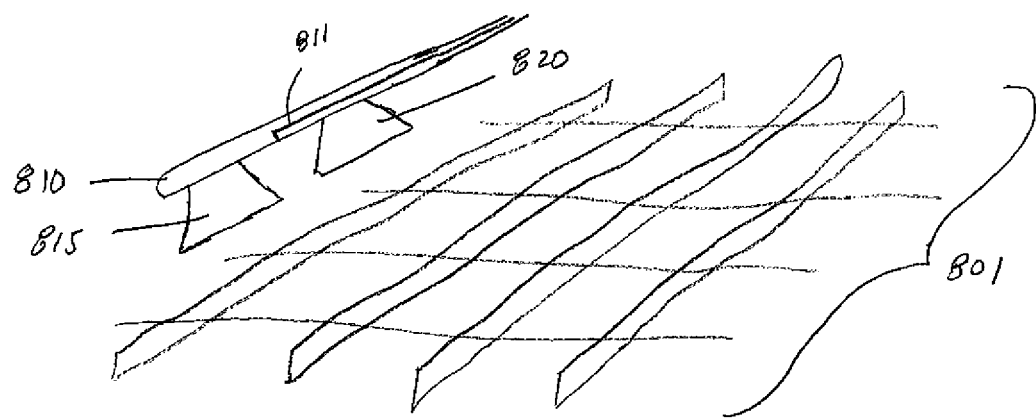
FIG. 8 includes an embodiment of the invention for removing biofilm.

FIG. 8 includes an embodiment of the invention that may be used alone or in conjunction with other embodiments described herein. For example, a mesh or grid 801 similar to other devices described herein may be used. Such a guard may be used to ensure ablation does not impede too closely on bone. In conjunction or independent of such ablation, wand 810 may couple to a debriding surface, such as brush devices 815, 820. Manual manipulation of wand 810 (while mesh or grid 801 remains stationary) may help clean, in a debriding fashion, biofilms and/or diseased tissue that projects inside or close to grid 801. In some embodiments brush devices 815, 820 may be coupled to an energy source to provide for their oscillation and or rotation to aid in cleaning. Wand 810 may include a conduit or lumen 811 with which to add and remove fluid, such as temperature modulated saline and/or add medications (e.g., having high, low, or medium viscosity yet still being considered fluid). Thus ablation can be achieved via a combination of electrical and mechanical energy.

An embodiment may include a kit having differently sized devices. For example, the user may select a size based on image measurements (e.g., fluoroscopy, CT scan, and the like) and based on the sinus being operated on (e.g., maxillary, frontal, sphenoid, and ethmoid). Thus, one device may have an outer guard cage that expands to a first maximum volume while another device may include an outer guard cage that expands to a larger second maximum volume.

Figure 7:
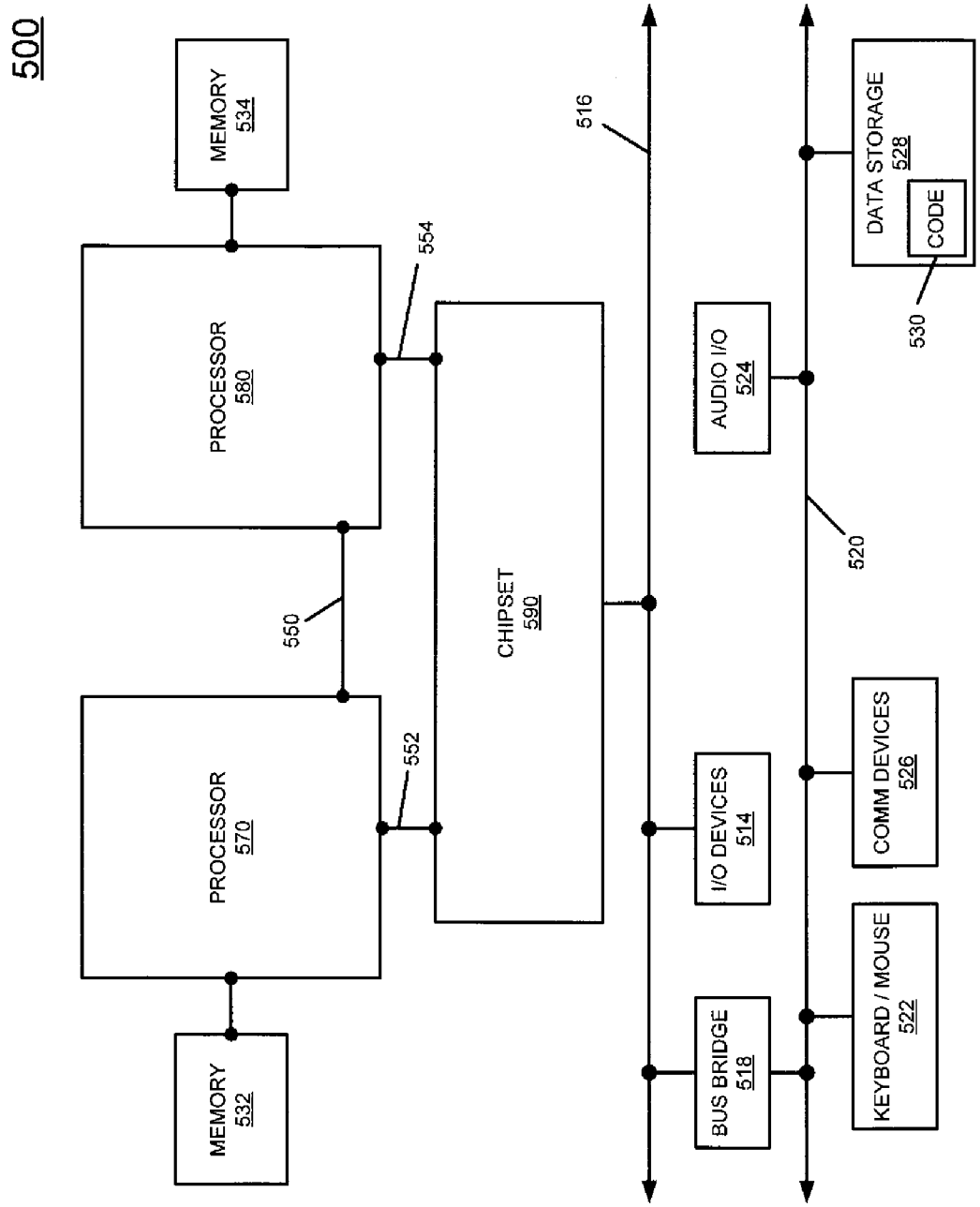
FIG. 7 includes a processing system for use with embodiments of the invention.

Embodiments may be implemented in many different system types. Referring now to FIG. 7, shown is a block diagram of a system in accordance with an embodiment of the present invention. Multiprocessor system 500 is a point-to-point interconnect system, and includes a first processor 570 and a second processor 580 coupled via a point-to-point interconnect 550. Each of processors 570 and 580 may be multicore processors. The term "processor" may refer to any device or portion of a device that processes electronic data from registers and/or memory to transform that electronic data into other electronic data that may be stored in registers and/or memory.

First processor 570 may include a memory controller hub and point-to-point (P-P) interfaces. Similarly, second processor 580 may include a MCH and P-P interfaces. The MCHs may couple the processors to respective memories, namely a memory 532 and a memory 534, which may be portions of main memory (e.g., a dynamic random access memory (DRAM)) locally attached to the respective processors. First processor 570 and second processor 580 may be coupled to a chipset 590 via P-P interconnects, respectively. Chipset 590 may include P-P interfaces.

Furthermore, chipset 590 may be coupled to a first bus 516 via an interface. Various input/output (I/O) devices 514 may be coupled to first bus 516, along with a bus bridge 518, which couples first bus 516 to a second bus 520. Various devices may be coupled to second bus 520 including, for example, a keyboard/mouse 522, communication devices 526, and data storage unit 528 such as a disk drive or other mass storage device, which may include code 530, in one embodiment. Further, an audio I/O 524 may be coupled to second bus 520.

Embodiments may be implemented in code and may be stored on a storage medium having stored thereon instructions which can be used to program a system to perform the instructions. The storage medium may include, but is not limited to, any type of disk including floppy disks, optical disks, optical disks, solid state drives (SSDs), compact disk read-only memories (CD-ROMs), compact disk rewritables (CD-RWs), and magneto-optical disks, semiconductor devices such as read-only memories (ROMs), random access memories (RAMs) such as dynamic random access memories (DRAMs), static random access memories (SRAMs), erasable programmable read-only memories (EPROMs), flash memories, electrically erasable programmable read-only memories (EEPROMs), magnetic or optical cards, or any other type of media suitable for storing electronic instructions.

Embodiments of the invention may be described herein with reference to data such as instructions, functions, procedures, data structures, application programs, configuration settings, code, and the like. When the data is accessed by a machine, the machine may respond by performing tasks, defining abstract data types, establishing low-level hardware contexts, and/or performing other operations, as described in greater detail herein. The data may be stored in volatile and/or non-volatile data storage. For purposes of this disclosure, the terms "code" or "program" cover a broad range of components and constructs, including applications, drivers, processes, routines, methods, modules, and subprograms. Thus, the terms "code" or "program" may be used to refer to any collection of instructions which, when executed by a processing system, performs a desired operation or operations. In addition, alternative embodiments may include processes that use fewer than all of the disclosed operations, processes that use additional operations, processes that use the same operations in a different sequence, and processes in which the individual operations disclosed herein are combined, subdivided, or otherwise altered.

While the present invention has been described with respect to a limited number of embodiments, those skilled in the art will appreciate numerous modifications and variations therefrom. It is intended that the appended claims cover all such modifications and variations as fall within the true spirit and scope of this present invention.

What is claimed is:

1. A method comprising:
   inserting a wand into a patient's sinus that has a diseased mucosal lining covering bone;
   expanding the wand inside the sinus by deploying first and second guard members, each of the first and second guard members being coupled to the wand;
   connecting outer portions of the first and second guard members respectively with first and second portions of the mucosal lining to directly compress the first and second portions of the mucosal lining against the bone so a third portion of the mucosal lining, which is not directly compressed by any guard member, lays between the compressed first and second portions of the mucosal lining; and
   while compressing the first and second portions of the mucosal lining, simultaneously (a) ablating the third portion of the mucosal lining with an ablation electrode, coupled to the wand, and (b) maintaining the outer portions of the first and second guard members between an outer portion of the ablation electrode and the bone to preserve the bone.

2. The method of claim 1 including inserting the wand through the patient's sinus ostium, past the ucinate process area, into the maxillary sinus, and then ablating the third portion of the mucosal lining.

3. The method of claim 1, wherein the first guard member is included in a first spline coupled to the wand and the second guard member is included in a second spline coupled to the wand, and the method further includes expanding the first and second splines within the sinus.

4. The method of claim 1, wherein the first and second guard members are included in a mesh and the method further includes deploying and expanding the mesh only after inserting the mesh inside the sinus.

5. The method of claim 1, wherein the wand couples to a sinuplasty balloon and the method further includes expanding the sinuplasty balloon in the patient's sinus ostium to expand the sinus ostium.

6. The method of claim 1, wherein the first and second guard members are included in a window and the third portion of the mucosal lining projects, at least partially, through the window and toward the ablation electrode while ablating the third portion of the mucosal lining.

7. The method of claim 1, wherein the third portion of the mucosal lining includes one of a polyp and chronically diseased sinus lining.

8. The method of claim 3, wherein the ablation electrode is included on a surface of a balloon, and the method further comprises:
   fully expanding the balloon entirely within the expanded first and second splines; and
   preventing the balloon from expanding outside the outer portions of the first and second guard members.

9. The method of claim 1, wherein the deployed first and second guard members are separated from each other by a maximum first breadth and the ablation electrode includes a maximum second breadth greater than the maximum first breadth to ensure the ablation electrode cannot pass between the deployed first and second guard members and ablate too closely to the bone.

10. The method of claim 1 including pressing the ablation electrode against inner portions of the first and second guard members while ablating the third portion of the mucosal lining.

11. The method of claim 1 comprising:
    contacting the ablation electrode to one of the first and second guard members; and
    automatically discontinuing ablating the third portion of the mucosal lining upon contacting the ablation electrode to the one of the first and second guard members.

12. The method of claim 1 comprising:
    expanding the wand inside the sinus by deploying a third guard member that is coupled to the wand;
    connecting an outer portion of the third guard member with a fourth portion of the mucosal lining to directly compress the fourth portion of the mucosal lining against the bone so a fifth portion of the mucosal lining, which is not directly compressed by any guard member, lays between the compressed fourth and second portions of the mucosal lining;
    while compressing the fourth and second portions of the mucosal lining, simultaneously ablating the third and fifth portions of the mucosal lining with one or more of the ablation electrode and an additional ablation electrode, the additional ablation electrode coupled to the wand.

13. The method of claim 12 comprising ablating the third portion of the mucosal lining, located away from the superior sinus wall, at a first energy level and ablating the fifth portion of the mucosal lining, located along the superior sinus wall, at a second energy level lower than the first energy level.

14. The method of claim 12, wherein the third and fifth portions of the mucosal lining are collectively included in a diffuse diseased mucosal lining.

15. The method of claim 1 comprising guiding the ablation electrode along a track, included in the wand, until the ablation electrode contacts one of the first and second guard members.

16. The method of claim 10, wherein the first guard member is longer than 0.5 mm and the first and second guard members are low energy conducting insulators, and the method further includes ablating the third portion of the mucosal lining without aid of simultaneous endoscopic visualization.

17. The method of claim 1 including sensing the ablation electrode is in contact with the third portion of the mucosal lining before ablating the third portion of the mucosal lining.

18. An apparatus comprising:
    a wand;
    first and second guard members coupled to the wand; and
    an ablation electrode coupled to the wand;
    wherein the wand is configured so (a) in a first position the wand is compressed to slide within a patient's nasal passage; and (b) in a second position the wand is located in the patient's sinus and the first and second guard members are expanded to connect outer portions of the first and second guard members respectively with first and second portions of the mucosal lining to directly compress the first and second portions of the mucosal lining against the bone so a third portion of the mucosal lining, which is not directly compressed by any guard member, lays between the compressed first and second portions of the mucosal lining while a user simultaneously (i) ablates the third portion of the mucosal lining with an ablation electrode, coupled to the wand, and (ii) maintains the outer portions of the first and second guard members between an outer portion of the ablation electrode and the bone to preserve the bone.

19. The apparatus of claim 18, wherein the first guard member is included in a first spline coupled to the wand and the second guard member is included in a second spline coupled to the wand.

20. The apparatus of claim 19, wherein the ablation electrode is included on a surface of a balloon so when the balloon is fully expanded the expanded balloon fits entirely within the expanded first and second splines and is prevented from deploying outside the outer portions of the first and second guard members.

21. The method of claim 3, wherein the ablation electrode is included in an array of electrodes on a surface of a balloon, and the method further comprises simultaneously expanding the balloon and deploying the first and second guard members, the first and second guard members being fixedly coupled to the balloon.

22. The method of claim 3 including:
- abrading the sinus with a brush coupled to the wand; and
- applying a fluid to the sinus via a lumen coupled to the wand.

\* \* \* \* \*